US006658297B2

(12) United States Patent
Loeb

(10) Patent No.: US 6,658,297 B2
(45) Date of Patent: Dec. 2, 2003

(54) METHOD AND APPARATUS FOR CONTROL OF BOWEL FUNCTION

(75) Inventor: Gerald E. Loeb, Pasadena, CA (US)

(73) Assignee: Alfred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 18 days.

(21) Appl. No.: 09/949,424

(22) Filed: Sep. 7, 2001

(65) Prior Publication Data

US 2002/0072779 A1 Jun. 13, 2002

Related U.S. Application Data

(60) Provisional application No. 60/232,753, filed on Sep. 15, 2000, and provisional application No. 60/230,664, filed on Sep. 7, 2000.

(51) Int. Cl.⁷ .................................................. A61N 1/18
(52) U.S. Cl. ......................................... 607/40; 600/547
(58) Field of Search ................... 607/40, 133; 600/547, 600/29, 30

(56) References Cited

U.S. PATENT DOCUMENTS

| 4,134,408 A | * | 1/1979 | Brownlee et al. .............. 607/33 |
| 5,193,539 A | | 3/1993 | Schulman et al. |
| 5,193,540 A | | 3/1993 | Schulman et al. |
| 5,312,439 A | | 5/1994 | Loeb |
| 5,324,316 A | | 6/1994 | Schulman et al. |
| 5,405,367 A | | 4/1995 | Schulman et al. |
| 5,423,872 A | | 6/1995 | Cigaina |
| 5,697,076 A | | 12/1997 | Troyk et al. |
| 5,836,994 A | | 11/1998 | Bourgeois |
| 5,861,014 A | | 1/1999 | Familoni |
| 5,995,872 A | | 11/1999 | Bourgeois |
| 6,051,017 A | | 4/2000 | Loeb et al. |
| 6,061,596 A | | 5/2000 | Richmond et al. |
| 6,104,955 A | * | 8/2000 | Bourgeois .................. 607/40 |
| 6,238,423 B1 | | 5/2001 | Bardy |
| 6,240,316 B1 | | 5/2001 | Richmond et al. |
| 6,327,503 B1 | * | 12/2001 | Familoni .................. 607/40 |
| 6,345,202 B2 | | 2/2002 | Richmond et al. |

OTHER PUBLICATIONS

Aizawa, M. Optical fiber electrodes for electrochemical luminescence–based homogeneous immunoassay. In Biosensor Technology Fundamentals and Applications. R.P. Buck et al., editors. New York: Marcel Dekker, Inc., pp. 209–218.

Abdel–Latif, M.S. Fiber optic–based biosensors utilizing immobilized enzyme systems. In Biosensor Technology Fundamentals and Application. R.P. Buck et al., editors. New York: Marcel Dekker, Inc., pp. 285–298.

Bellahsene, B.–E. et al. Acceleration of gastric emptying with electrical stimulation in a canine model of gastroparesis. 1992. American Journal of Physiology 226: G826–G834.

Fontana, R.J. et al. Jejunostomy tube placement in refractory diabetic gastroparesis: A retrospectifve review. 1996. The American Journal of Gastroenterology 91:2174–2178.

Garry, R.C. et al. Reflexes involving the external urethral sphincter in the cat. J. Physiol. 1959. vol. 149: pp. 653–665.

Gems Study Group. Electrical stimulation for the treatment of gastroparesis—preliminary repor of a multicenter international trial. (Abstract.) 1996. Gastroenterology 10(4): A668.

(List continued on next page.)

Primary Examiner—Jeffrey R. Jastrzab
(74) Attorney, Agent, or Firm—McDermott, Will & Emery

(57) ABSTRACT

Spinal cord injury and other injuries and diseases of the nervous system often result in the inability to sense the need to empty the rectum or to control the timing of bowel movements. This invention includes microminiature electronic devices implanted on or around the large bowel to sense the volume and nature of rectal contents and to stimulate peristaltic contractions to empty the large bowel when it is convenient for the patient to do so.

68 Claims, 2 Drawing Sheets

OTHER PUBLICATIONS

Gems Study Group. Long–term results of gastric stimulation four times higher than the slow wave frequency in patients with drug–refractory gastroparesis. (Abstract.) 1999. Gastroenterology 116: G4131.

Goswami, K, et al. Fiber optic chemical sensors (FOCS): An answer to the need for small, specific monitors. In Biosensor Technology Fundamentals and Applications. R.P. Buck et al., editors. New York: Marcel Dekker, Inc., pp. 299–310.

Hasler, W.L. Editorial: The brute force approach to electrical stimulation of gastric emptying: A future treatment of refractory gastroparesis? 2000 Gastroenterology 118: 433–436.

Janssens, J. et al. Improvement of gastric emptying in diabetic gastroparesis by erythromycin. 1990. The New England Journal of Medicine 322: 1028–1031.

Luo, J. et al. Gastric electrical stimulation improves both GI symptoms and gastric empty in patients with "post–surgical" gastroparesis. (Abstract.) 1999. Gastroenterology 116: S0162.

McCallum, R.W. et al. Gastric pacing improves emptying and symptoms in patients with gastroparesis. Gastroenterology 1998; vol. 114: pp. 456–461.

Mintchev, M. et al. Computer model of gastric electrical stimulation. 1997. Annals of biomedical engineering 25: 726–730.

Snape, W.J., Jr. et al. Metoclopramide to treat gastroparesis due to diabetes mellitus: A double–blind, controlled trial. 1982. Annals of internal medicine 96:444–446.

Sturm, A. et al. Treatment of patients with gastroparesis: A meta–analysis of prokinetics. (Abstract.) 1997. Gastroenterology 112:A833.

Tabbaa, M. et al. Gastric electrical stimulation rapidly improves nutritional depletion in gastroparesis. (Abstract.) 1999. Gastroenterology 116:G2543.

Tack, J. et al. The influence of gastric electrical stimulation on proximal gastric motor and sensory function in severe idiopathic gastroparesis. 1999. Gastroenterology 116:G4733.

* cited by examiner

METHOD AND APPARATUS FOR CONTROL OF BOWEL FUNCTION

RELATED APPLICATIONS

This application claims the filing date benefit of U.S. Provisional Application No. 60/230,664, filed on Sep. 7, 2000, entitled "Method and Apparatus for Control of Bowel Functions", and of U.S. Provisional Application No. 60/232,753, filed on Sep. 15, 2000, entitled "Method and Apparatus to Treat Disorder of Gastrointestinal Peristalsis", the contents of which are incorporated herein.

FIELD OF THE INVENTION

This application relates to systems and methods for controlling bowel function, particularly for patients with spinal injury or diseases of the nervous system.

BACKGROUND OF THE INVENTION

There are various surgical procedures and hydraulic implants that have been developed to provide fecal continence in cases of inadequate anal sphincter strength. Electrical stimulators for the spinal cord and sacral roots have also been used to stimulate emptying of the rectum. See previously granted patents for the microstimulator implants themselves and for certain applications including therapeutic electrical stimulation (TES) to strengthen urinary and anal sphincter muscles, which are incorporated herein by reference. U.S. Pat. Nos. 5,312,439, 5,697,076, 6,061,596, 5,324,316, 5,405,367, 6,051,017, 5,193,540, and 5,193,539 incorporated by reference in their entirety.

One of the hallmarks of social animals is the ability to control when and where they relieve themselves of solid waste products of digestion as feces. The so-called "bowel movement" is the last step in a complex series of processes whereby food is successively processed, stored and moved along successive stages of the digestive tract. These steps are normally controlled by a complex system of smooth muscles, which are under the control of the autonomic nervous system. Humans with intact nervous systems have limited conscious awareness of these processes, but they do sense distension at the various loci in the gastrointestinal track and adjust their behavior accordingly. Distension produced by accumulation of fecal material in the rectum gives rise to the feeling that a bowel movement is imminent, permitting the person either to go to a place where it is socially acceptable to empty the bowels or to block the expulsion of feces at least temporarily by voluntarily contracting the external anal sphincter.

If the spinal cord is defective, which may result from spinal cord injury, tumors or birth defects, then various of the steps of peristaltic motion, conscious sensation, and voluntary control may be absent or abnormal. This gives rise to various problems of constipation and incontinence that interfere with the health of such patients and their ability to participate in normal social activities. Many such patients spend an inordinate amount of time each day attempting to empty their bowels by various maneuvers and in the absence of any clear indication of whether and when this is necessary or complete.

SUMMARY OF THE INVENTION

The present invention therefore provides methods and apparatus for controlling bowel function. This invention includes microminiature electronic devices implanted on or around the large bowel to sense the volume and nature of rectal contents and to stimulate peristaltic contractions to empty the large bowel when it is convenient for the patient to do so.

It is an object of the present invention to detect peristaltic motion and distension of the rectum.

It is a further object of the present invention to determine whether said rectal distension has resulted from accumulation of solid, liquid or gaseous material.

It is still a further object of the present invention to permit a patient to electrically trigger peristaltic motion upon command in order to effect defecation.

In one embodiment of the present invention, one or more microelectrical implants are injected into the walls or surgically implanted onto the serosal surface of the rectum and descending colon, where they sense motion and distension of those structures and can generate electrical impulses that stimulate peristaltic contractions. External control is also included, which transmits power and command signals to the microelectrical implants and receives sensed information from them by means of an inductive coil upon which the patient sits.

DETAILED DESCRIPTION OF THE INVENTION

Figure 1:
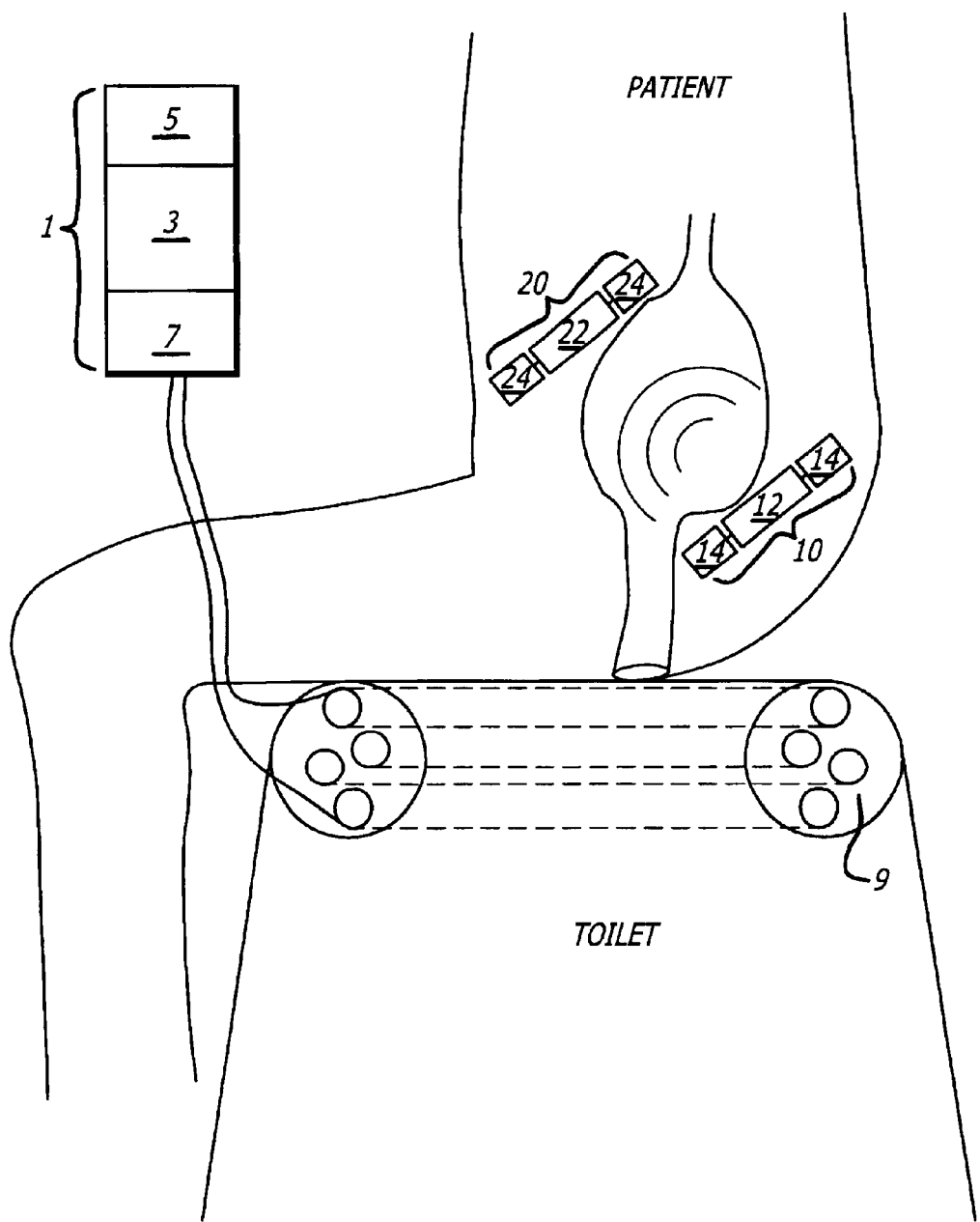
FIG. 1 illustrates exemplary embodiments of internal and external electronic devices used in the present invention.

Referring to FIG. 1, an external electronic device 1 is coupled to an inductive coil 9 upon which the patient is sitting. A first implanted electronic device 10 and a second implanted electronic device 20 are placed in the walls of the rectum or on the serosal surface of the rectum. These first and second implanted electronic devices perform both detection and triggering functions. The inductive coil 9 may be removably coupled to a toilet. It may also be removably coupled to a seat cushion or a mattress.

The first and second implanted electronic devices 10 and 20 each comprise a hermetically sealed capsule 12 and 22 in which electronic circuitry is located. Attached to the hermetically sealed capsules 12 and 22 are two electrodes 14 and 24. The electronic circuitry may include an inductive coil, power storage capacitor, and integrated circuit for performing various functions as detailed below and illustrated schematically in FIG. 2.

The external electronic device 1 transmits power and command signals to implanted electronic devices 10 and 20 by creating a modulated radio frequency (RF) field on the inductive coil 9. The modulated radio frequency field may be created using a variant of a Class E power oscillator 7 called "suspended carrier transmission". In this scheme, a very high Q resonant circuit (Q>100) consisting of inductive coil 9 and a tuning capacitor can be energized to a high level of inductive field strength while drawing only a small current from a power supply. When the peak sustained oscillations have been achieved in inductive coil 9, the carrier may be 100% modulated in fewer than four carrier cycles by opening a switch in the circuit between the tuning capacitor and the coil at precisely the instant when the current through the coil is zero and the voltage on the capacitor is maximal. The carrier can be reinstated rapidly and with minimal energy loss by closing the switch. The number of cycles in which the carrier is on or off can be used to encode digital data for the purpose of controlling the implanted electronic devices 10 and 20. When the switch is open and the carrier is off, inductive coil 9 can be used as a high impedance antenna to detect outgoing emissions that encode information from implanted electronic devices 10 and 20.

The implanted electronic devices 10 and 20 may be used as a pair to perform different types of measurements. In one embodiment, the implanted electronic devices measure physical distension of the rectum. The implanted electronic device 10 emits a short burst of RF energy upon command from external electronic means 1, at a time at which the suspended carrier is in the off state. The implanted electronic device 20 detects the strength of the short burst of RF energy emitted by the implanted electronic device 10, which depends on the physical orientation and distance between the two implanted electronic devices. By locating the implanted electronic devices on opposite sides of the rectum, the strength of the RF coupling between the two devices will reflect distension of the rectum.

In another embodiment, the implanted electronic devices measure the electrical resistance of the material in the rectum. The implanted electronic device 10 emits a brief electrical current from its two electrodes 14. The implanted electronic device 20 detects the strength of the electrical field created in the adjacent tissues via its two electrodes 24 which are connected to an amplifier and a digitizer. The field strength depends on the dimensions and electrical conductivity of the material separating the two implanted electronic devices. Solid fecal material has an electrical conductivity that is midway between liquids (high electrical conductivity) and gases (low electrical conductivity).

The results of the two measurements described in the embodiments above are transmitted to the external electronic controller 1 which uses the information about distance and electrical coupling to infer both the amount and the nature of the rectal distension. This information can be presented to the patient through an interface 5, whereupon the patient decides if and when it is necessary to empty the rectum. In the event that the patient decides to empty the bowels, this is conveyed through interface 5 to a controller 3 which transmits commands to one or both of the implanted electronic devices that cause them to emit electrical current pulses sufficiently strong to trigger peristaltic contractions of the rectum.

The implanted electrical devices 10 and 20 may also include an electrical stimulator implanted into the tissues of rectoanal region to facilitate the emptying of the rectum. The implanted electrical devices 10 and 20 may also include an electrical stimulator that activates a plurality of preganglionic parasymapathetic neurons to trigger defecation. The implanted electrical devices 10 and 20 may also include an electrical stimulator that activates a plurality of perianal cutaneous afferents that activate spinal reflexes to trigger defecation.

Figure 2:
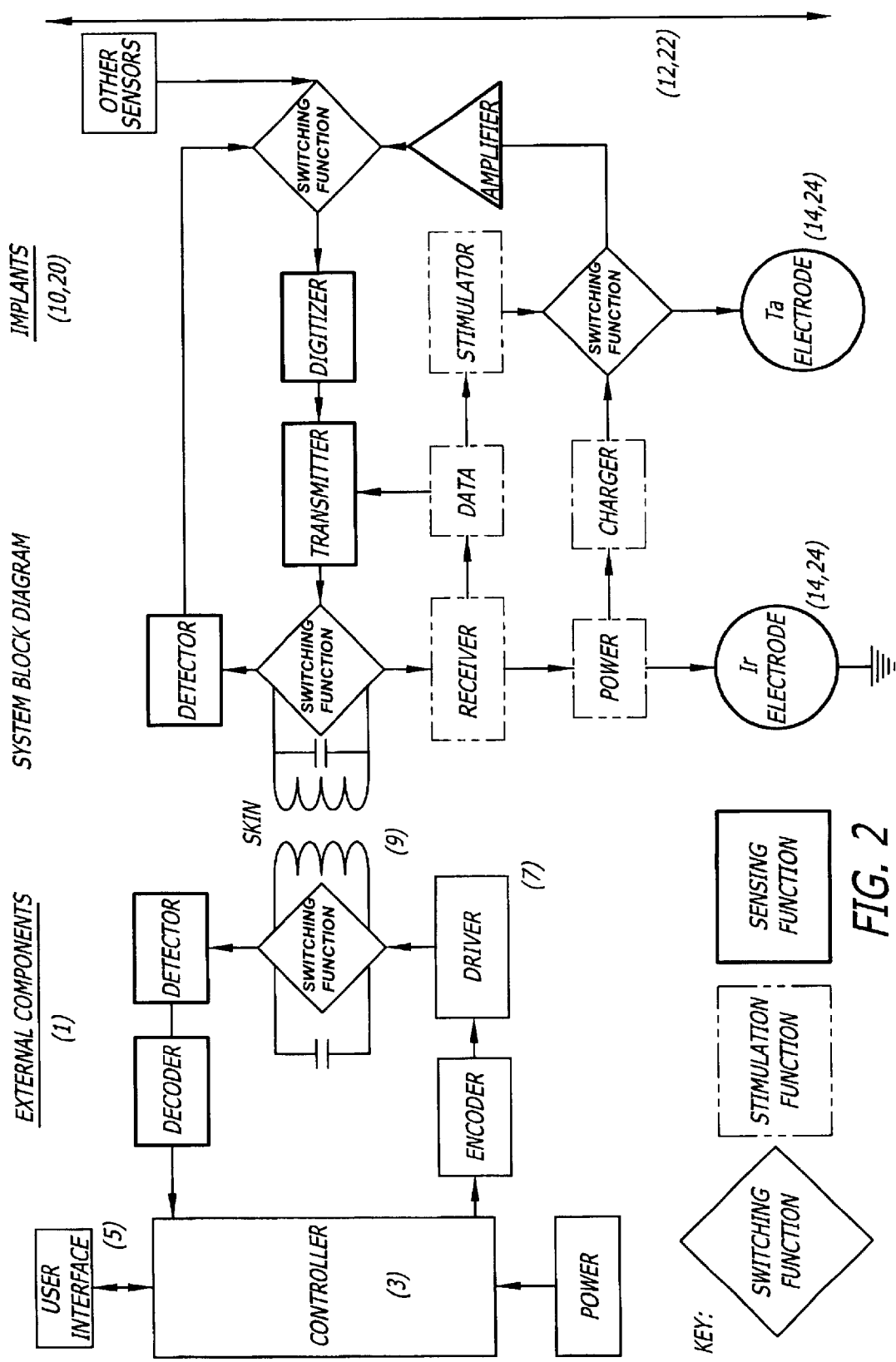
FIG. 2 is a block diagram of the components of both the external electronic devices and the internal electronic devices.

FIG. 2 provides a more complete block diagram of the electronic functions performed by circuitry within the external and implanted components in order to support the operations described above. In particular, it depicts an embodiment in which a single type of implant can perform a multitude of functions upon command from the external components. It will be obvious to one skilled in the art that these electronic functions may be divided into two or more types of more specialized implants.

Referring to FIG. 2, the external components 1 may be subdivided into functional blocks as follows. The user interface 5 provides a display whereby the user can see the results of the measurements in a simplified form upon which he/she can base decisions about self care and control. The user can instruct the system to begin or terminate self-care functions such as stimulating the evacuation of the rectum.

The controller 3 includes all digital circuitry required to operate the remainder of the system, including storage devices that are loaded with and retain information specific to the patient and the implanted components, such as calibrations for the sensors and stimulus parameters required to perform self-care functions.

Power can be provided by AC/DC converter, batteries, or any other suitable device.

Communication with the implanted electronic devices is achieved by inductive coupling between the external inductive coil 9 and inductive coils contained within each implant.

A driver 7 uses Class E circuitry to create a sufficiently high field strength of the RF carrier signal produced in external inductive coil 9 so that the voltage generated in each implant's inductive coil is sufficient to power the electronic circuitry in that implant. A tuning capacitor plus the external inductive coil 9 form a resonantly tuned tank circuit with a high Q.

An encoder formats the digital command information from the controller 3 to each implant so that it can be applied to the driver 7 in order to modulate the RF carrier signal so as to convey that command information to the implants.

After commanding an implant to transmit out sensor data, the controller 3 must stop the transmission of RF power from the external inductive coil 9 by opening an electronic switch in the tank circuit at approximately the phase in the RF oscillation when the field strength in inductive coil 9 passes through zero. This causes inductive coil 9 to act like a high impedance antenna for the much weaker RF oscillations produced by the implant that is transmitting said sensor data by amplitude modulation of this outgoing RF signal.

A detector circuit amplifies and conditions the outgoing RF signal as picked up by the inductive coil 9 acting as an antenna.

A decoder circuit converts the amplitude fluctuations in the outgoing RF signal into digital data representing the sensor data, which is then processed by the controller 3.

Referring to FIG. 2, the implanted electronic devices 10 and 20 may each be subdivided in functional blocks as follows. The implant electronic circuitry 10 and 20 is contained within the hermetically sealed capsule 12 and 22 that protects it from moisture. It is connected to a pair of electrodes 14 and 24 affixed outside the package so as to make electrical contact with the body tissues.

One primary role for the received digital data is to specify the strength and timing of electrical pulses emitted through electrodes 14 and 24, as controlled by the stimulator function. When stimulation pulses are not being emitted but an RF carrier signal is being received, power extracted from the carrier is stored by on the electrodes themselves by the charger. The Ta electrode is pre-anodized to approximately four times the maximal DC voltage produced by the power and charger circuitry so that it acts as an electrolytic storage capacitor with respect to the electrically conductive bodily fluids surrounding the electrode. This permits relatively larger amounts of power to be stored and released in the form of intense, brief, intermittent stimulation pulses.

One primary role for the received digital data is to specify the strength and timing of electrical pulses emitted through electrodes 14 and 24, as controlled by the stimulator function. When stimulation pulses are not being emitted but an RF carrier signal is being received, power extracted from the carrier is stored by on the electrodes themselves by the charger. The Ta electrode is pre-anodized to approximately four times the maximal DC voltage produced by the power and charger circuitry so that it acts as an electrolytic storage capacitor with respect to the electrically conductive bodily fluids surrounding the electrode. This permits relatively large amounts of power to be stored and released in the form of intense, brief, intermittent stimulation pulses.

The electrodes 14 and 24 can also be disconnected from both the charger and stimulator circuitry and connected to an amplifier circuit that amplifies and conditions potentials present on the electrodes. Thus, when one implant is generating a stimulus pulse, another implant can measure the strength of the potential field created in its vicinity by the stimulus pulse, the field strength of which will depend on the nature and thickness of the tissue intervening between the two implants.

The amplified signal from the electrodes or a signal from another sensor that may be included is switched to the digitizer which produces digital data corresponding to the amplitude of the sensor signal. The digitized sensor data is used to modulate a transmitter which causes the resonant circuit to emit an outgoing RF telemetry signal that is received by the external inductive coil and its related detector and decoder circuitry. During this transmission, the external circuitry stops transmitting its RF carrier signal.

When one implant is generating an outgoing RF telemetry signal, one or more other implants in its vicinity can be commanded to act as sensors of the strength of the RF signal in their vicinity. The RF signal picked up by an implant that is functioning as an RF field sensor is amplified and conditioned by the detector circuit and conveyed to the digitizer for later transmission outward.

It is to be understood that other embodiments may be utilized and structural and functional changes may be made without departing from the respective scope of the present invention. The attached description of exemplary and anticipated embodiments of the invention have been presented for the purposes of illustration and description. They are not intended to be exhaustive or to limit the invention to the precise forms disclosed. Many modifications and variations are possible in light of the teachings herein.

I claim:

1. A system for controlling bowel function, the system comprising:
   a first electronic device adapted to be implanted in the body and to detect distension of the rectum;
   a second electronic device adapted to be implanted in the body and to trigger peristaltic evacuation of the bowel; and
   an external electronic device coupled to an inductive coil.

2. The system of claim 1 wherein the first and second electronic devices measure the distance between the first and second electronic devices by emitting an electromagnetic field and measuring the strength of the electromagnetic field.

3. The system of claim 2 wherein the first and second electronic devices measure the electrical coupling provided by a material between the first and second electronic devices by emitting an electrical current and measuring the strength of a potential field.

4. The system of claim 3 wherein the external electronic device computes an electrical resistance of the material between the first and second electronic devices.

5. The system of claim 1 further comprising an electrical stimulator adapted for implantation in a rectoanal region.

6. The system of claim 5 further comprising an electrical stimulator for activating a plurality of preganglionic parasympathetic neurons to trigger defecation.

7. The system of claim 5 further comprising an electrical stimulator for activating a plurality of perianal cutaneous afferents to activate spinal reflexes to result in defecation.

8. The system of claim 5 wherein the external electronic device includes an interface to permit activation of the electrical stimulator.

9. The system of claim 1 wherein the first and second implanted electronic devices receive power and command signals by an electromagnetic coupling to the external electronic device.

10. The system of claim 9 wherein a class E electronic power oscillator that is 100% modulated in fewer than four carrier cycles electromagnetically couples the first and second electronic devices and the external electronic device.

11. The system of claim 9 wherein the inductive coil electromagnetically couples the first and second electronic devices and the external electronic device.

12. The system of claim 1 wherein the first and second electronic devices communicate with the inductive coil.

13. The system of claim 12 wherein the inductive coil is removably coupled to a toilet.

14. The system of claim 12 wherein the inductive coil is removably coupled to a seat cushion.

15. The system of claim 12 wherein the inductive coil is removably coupled to a mattress.

16. A method for determining the state of material in the rectum by measuring the electrical resistance of the material in the rectum, the method comprising:
   implanting first and second microelectrical devices in the rectal walls so as to stimulate peristaltic contractions; and
   emitting a brief electrical current from the first microelectrical device; and measuring the strength of the electrical field at the second microelectrical device.

17. A method for determining the state of material in the rectum by measuring the electrical resistance of the material in the rectum, the method comprising:
   implanting first and second microelectrical devices in the rectal walls;
   emitting a brief electrical current from the first microelectrical device;
   measuring the strength of the electrical field at the second microelectrical device; and
   transmitting the measurement recorded at the second microelectrical device to an external controller which uses information about the distance and electrical coupling of the first and second microelectronic devices to infer the resistance and nature of the material in the rectum.

18. The method of claim 17, wherein the first electronic device and the second electronic device are configured to be separately positionable in the body.

19. The device of claim 17, wherein first and second electronic devices are adapted for positioning by injection.

20. A method for measuring physical distension of the rectum, the method comprising:
   implanting first and second microelectrical devices in the rectal walls so as to stimulate peristaltic contractions; and
   emitting a short burst of RF energy from the first microelectrical device;
   and measuring the strength of the short burst of RF energy at the second microelectrical device.

21. A method for measuring physical distension of the rectum, the method comprising:
   implanting first and second microelectrical devices in the rectal walls so as to stimulate peristaltic contractions;
   emitting a short burst of RF energy from the first microelectrical device;
   measuring the strength of the short burst of RF energy at the second microelectrical device; and
   transmitting the measurement recorded at the second microelectrical device to an external controller which uses information about the distance and electrical coupling of the first and second microelectronic devices to infer the amount and nature of the rectal distention.

22. The method of claim 21, wherein the first electronic device and the second electronic device are configured to be separately positionable in the body.

23. The device of claim 21, wherein first and second electronic devices are adapted for positioning by injection.

24. The method of claim 21, wherein the electromagnetic field is a radiofrequency field.

25. A device for use in detecting the state of material in the body by measuring the electrical resistance of the material, comprising:
   a) a first electronic device for generating an electrical current, the first electrical device adapted for implantation in the body;
   b) a second electronic device configured to detect a potential field, the second electrical device adapted for implantation in the body;
   c) an external electronic device in communication with the second electronic device for detecting a signal indicative of the strength of the potential field detected by the second electrical device, the external electronic device using the signal to determine the state of material between the first and second electrical devices.

26. The device of claim 25, wherein the external electronic device is electromagnetically coupled to the first electronic device and second electronic device by an inductive coil.

27. The device of claim 25, wherein the first electronic device comprises a first capsule in communication with two electrodes and wherein the second electronic device comprises a capsule in communication with two electrodes.

28. The device of claim 25, wherein the electronic device further comprises a user interface for displaying the results of measurements to a user.

29. The device of claim wherein the external electronic device further comprises a controller in communication with the first or second electronic devices, whereby activation of the controller causes the emission of an electrical current from the first or second electronic devices, and wherein the electrical current stimulates peristaltic contractions.

30. The device of claim 25, wherein the external electronic device further comprises a controller in communication with an electrical stimulator whereby activation of the controller causes the emission of an electrical current from the electronic device, and wherein the electrical current stimulates peristaltic contractions.

31. The device of claim 25, wherein the first electronic device and the second electronic device are separately positionable.

32. The device of claim 25, wherein the first electronic device is positioned on the opposite side of the bowel from the second electronic device.

33. The device of claim 25, wherein the first and second electronic devices are positioned in one location selected from the group comprising: the walls of the bowel, the serosal surface of the bowel, the walls of the rectum, or the serosal surface of the rectum.

34. The device of claim 25, wherein first and second electronic devices are adapted for positioning by injection.

35. The device of claim 24, wherein the external electronic device transmits power to the first or second electronic device by generating a modulated electromagnetic field.

36. The device of claim 25, wherein the external electronic device transmits command signals to the first or second electronic device by generating a modulated electromagnetic field.

37. The device of claim 25, wherein the external electronic device comprises:
   a) a user interface in operable communication with a controller;
   b) a driver for creating an electromagnetic signal; and
   c) optionally a detector for detecting electromagnetic signals.

38. The device of claim 35, further comprising an electrical stimulator configured for implantation in the proximity of one of the rectoanal region, a preganglionic parasympathetic neuron, or a perianal cutaneous afferent.

39. The device of claim 40, wherein the electromagnetic field is a radiofrequency field.

40. A device for use in detecting tissue distension by measuring mutual electromagnetic coupling, comprising:
   a) a first electronic device for generating an electromagnetic field, the first electrical device adapted for implantation in the body;
   b) a second electronic device configured to detect an electromagnetic field, the second electrical device adapted for implantation in the body; and
   c) an external electronic device in communication with the second electronic device for detecting a signal indicative of the strength of the electromagnetic field detected by the second electrical device, the external electronic device using the signal to determine the degree of tissue distention between the first and second electrical devices.

41. The device of claim 40, wherein the external electronic device is electromagnetically coupled to the first electronic device and second electronic device by an inductive coil.

42. The device of claim 40, wherein the first electronic device and the second electronic device are separately positionable.

43. The device of claim 40, wherein the first electronic device is positioned on the opposite side of the bowel from the second electronic device.

44. The device of claim 40, wherein the first and second electronic devices are positioned in one location selected from the group comprising: the walls of the bowel, the serosal surface of the bowel, the walls of the rectum, or the serosal surface of the rectum.

45. The device of claim 40, wherein first and second electronic devices are dared for positioning by injection.

46. The device of claim 40, wherein the external electronic device transmits power to the first or second electronic device by generating a modulated electromagnetic field.

47. The device of claim 40, wherein the external electronic device transmits command signals to the first or second electronic device by generating a modulated electromagnetic field.

48. The device of claim 40, wherein the external electronic device comprises:
   a) a user interface in operable communication with a controller;
   b) a driver for creating an electromagnetic signal; and
   c) optionally a detector for detecting electromagnetic signals.

49. The device of claim 40, further comprising an electrical stimulator configured for implantation in the proximity of one of the rectoanal region, a preganglionic parasympathetic neuron, or a perianal cutaneous afferent.

50. A device for use in the control of gastrointestinal function, comprising:
   a) an external electronic device for generating control signals;
   b) a first electronic device in communication with the external electronic device, including a component for emitting a signal to a second implanted electronic device; and
   c) the second electronic device in communication with the external electronic device, including a component for measuring a signal from the first implanted electronic device and communicating measurement information to the external electronic device;
   wherein the first and second implanted electronic devices are separably positionable and adapted for implantation in the proximity of the gastrointestinal system, and
   wherein the external electronic device determines the status of the gastrointestinal tract based on the measurement transmitted from the second electronic device.

51. A device for use in detecting the volume and resistivity of material in a body cavity comprising:
   a) a first pair of electronic devices adapted for implantation in the body comprising, including a first electronic device for generating an electrical current and a second electronic device configured to detect a potential field,
   b) a second pair of electronic devices adapted for implantation in the body, including a third electronic device for generating an electromagnetic field and a fourth electronic device configured to detect an electromagnetic field,
   c) an electronic device in communication with the second and fourth electronic devices for receiving a signal indicative of the strength of the potential field detected by the second electrical device, and for receiving a signal indicative of the strength of the electromagnetic field detected by the fourth electrical device, the electronic device using information received to infer the distance between the first and second electronic devices and the resistivity of the material.

52. A device for use in detecting the volume and resistivity of material in a body cavity comprising:
   a) a plurality of electronic devices adapted for implantation in the body comprising at least a first electronic device and a second electronic device;
   b) wherein one of the electronic devices is configured to generate an electrical current and the other electronic device is configured to detect a potential field; and
   c) an external electronic device in communication with the plurality of electronic devices receiving signals indicative of the strength of the potential field and electromagnetic field detected, the external electronic device using information received to infer the distance between the plurality of electronic devices and the resistivity of the material.

53. The device of claim 52, wherein the first electronic device comprises a first capsule in communication with two electrodes and wherein the second electronic device comprises a capsule in communication with two electrodes.

54. The device of claim 52, wherein the electronic device further comprises a user interface for displaying the results of measurements to a user.

55. The device of claim 52, wherein the external electronic device further comprises a controller in communication with at least one of the plurality of electronic devices adapted for implantation in the body, whereby a signal from the controller causes the emission of an electrical current from at least one of the plurality of electronic devices adapted for implantation in the body, and wherein the electrical current stimulates peristaltic contractions.

56. A device for use in detecting the state of material in the body by measuring the electrical resistance of the material, comprising at least three electronic devices configured for implantation into the body, wherein:
   a) a first electronic device is configured for generating an electrical current;
   b) a second electronic device is configured for generating an electromagnetic field;
   c) a third electronic device configured to detect a potential field and an electromagnetic field; and
   d) an external electronic device in communication with the third electronic device for receiving a signal indicative of the strength of the potential field and electromagnetic field detected by the third electrical device, the external electronic device using information received to infer the distance between the electrical devices and the resistivity of the material.

57. A device for use in detecting the state of material in the body by measuring the electrical resistance of the material, comprising:
   a) an external electronic device for generating control signals;
   b) an inductive coil operably connected to the external electronic device for transmitting control signals;
   c) a first electronic device adapted for implantation in the body including a first capsule having electronic circuitry in operable communication with a first antenna for detecting control signals, and the first capsule in communication with two electrodes for generating an electrical current; and
   d) a second electronic device adapted for implantation in the body including a second capsule having electronic circuitry and in communication with two electrodes for detecting the magnitude of the electronic field emitted from the first electronic device, and a second antenna for transmitting signals to the inductive coil;
   wherein the external electronic device computes an electrical resistance of the material between the first and second electronic devices from the signal detected at the second electronic device.

58. The device of claim 57, wherein the electromagnetic field is a radiofrequency field.

59. A device for use in detecting the state of material in the body by measuring the electrical resistance of the material, comprising:
   a) an external electronic device for generating control signals;
   b) an inductive coil operably connected to the external electronic device for transmitting control signals;
   c) a first electronic device configured for implantation in the body including a first capsule having electronic circuitry in operable communication with a first antenna for detecting control signals, and the first electronic device emitting an electromagnetic field; and d) a second electronic device configured for implantation in the body including a second capsule having electronic circuitry and detecting the magnitude of the electromagnetic field emitted from the first implanted electronic device, and a second antenna for transmitting signals to the inductive coil;

wherein the external electronic device computes the distention of the tissue between the first and second electronic devices from the signal detected at the second electronic device.

60. A method for use in detecting the state of material in a body cavity by measuring the electrical resistance comprising:

a) implanting a first and second electronic device, the first and second electronic devices configured for implantation into the body;

b) emitting electrical current from the first electronic device;

c) measuring the strength of the potential field at the second electronic device; and d) transmitting the measurement recorded at the second microelectrical device to an external controller which uses information about the strength of the potential field to infer the state of material in the body cavity.

61. The device of claim 60, wherein first and second electronic devices are adapted for positioning by injection.

62. The method of claim 60, further including positioning the first electronic device on the opposite side of the bowel from the second electronic device.

63. The method of claim 60, further comprising implanting an electrical stimulator into the gastrointestinal tract of a patient; and activating the electrical stimulator to elicit peristaltic contractions.

64. A method for measuring tissue distension, the method comprising:

a) separately implanting a first electronic device and a second electronic device at a distance from one another;

b) emitting an electromagnetic field from a first electronic device;

c) measuring the strength of the electromagnetic field at a second electronic device; and d) transmitting a signal corresponding to strength of the electromagnetic field at a second electronic device to an external electronic controller, the electronic controller using the signal to infer the magnitude of tissue distention.

65. The device of claim 64, wherein first and second electronic devices are adapted for positioning by injection.

66. The method of claim 64, further including positioning the first electronic device on the opposite side of the bowel from the second electronic device.

67. The method of claim 64, further comprising implanting an electrical stimulator into the gastrointestinal tract of a patient; and activating the electrical stimulator to elicit peristaltic contractions.

68. The method of claim 64, wherein the electromagnetic field is a radiofrequency field.

* * * * *